US012354756B2

(12) United States Patent
Naik et al.

(10) Patent No.: US 12,354,756 B2
(45) Date of Patent: Jul. 8, 2025

(54) SYSTEMS AND METHODS FOR DESIGNING VACCINES

(71) Applicant: Sanofi Pasteur, Inc., Swiftwater, PA (US)

(72) Inventors: Armaghan Waseem Naik, Cambridge, MA (US); Mario Barro, Reading, MA (US)

(73) Assignee: Sanofi Pasteur, Inc., Swiftwater, PA (US)

( * ) Notice: Subject to any disclaimer, the term of this patent is extended or adjusted under 35 U.S.C. 154(b) by 641 days.

(21) Appl. No.: 17/075,434

(22) Filed: Oct. 20, 2020

(65) Prior Publication Data

US 2021/0118575 A1 Apr. 22, 2021

Related U.S. Application Data

(60) Provisional application No. 62/924,096, filed on Oct. 21, 2019.

(51) Int. Cl.

| | |
|---|---|
| ***G16H 50/70*** | (2018.01) |
| ***A61K 39/00*** | (2006.01) |
| ***G16B 30/00*** | (2019.01) |
| ***G16B 40/00*** | (2019.01) |
| ***G16H 10/20*** | (2018.01) |
| ***G16H 50/20*** | (2018.01) |
| ***G16H 50/80*** | (2018.01) |
| ***G16H 70/40*** | (2018.01) |
| ***G16H 70/60*** | (2018.01) |

(52) U.S. Cl.

CPC ............. *G16H 50/70* (2018.01); *G16B 30/00* (2019.02); *G16B 40/00* (2019.02); *G16H 10/20* (2018.01); *G16H 50/20* (2018.01); *G16H 50/80* (2018.01); *G16H 70/40* (2018.01); *G16H 70/60* (2018.01); *A61K 39/00* (2013.01)

(58) Field of Classification Search

None

See application file for complete search history.

(56) References Cited

U.S. PATENT DOCUMENTS

2014/0052428 A1 2/2014 Naik et al.

FOREIGN PATENT DOCUMENTS

| | | |
|---|---|---|
| CA | 2826894 | 8/2012 |
| CN | 103493057 | 1/2014 |
| CN | 109448781 | 3/2019 |
| WO | WO 2012112534 | 8/2012 |

OTHER PUBLICATIONS

Cheng B. Proceedings of the 6th International Conference on Bioinformatics and Computational Biology, pp. 1-5. (Year: 2018).*

Heinson AI. Bioinformatics approaches to vaccine design for bacterial pathogens. University of Southampton, doctoral dissertation, 249 pgs. (Year: 2017).*

Adiloglu K. A machine learning approach to two-voice counterpoint composition. Knowledge-Based Systems 20: 30-309. (Year: 2007).*

Sanchez-Lengeling B. Inverse molecular design using machine learning: generative models for matter engineering. Science 361: 360-365. (Year: 2018).*

Gupta et al., "Identification of Immunogenic Consensus T-cell Epitopes in Globally Distributed Influenza-A H1N1 Neuraminidase", Infection, Genetics and Evolution, Oct. 2010, 11(2):308-319.

Huang et al., "Co-evolution Positions and Rules for Antigenic Variants of Human Influenza A/H3N2 Viruses", BMC Bioinformatics, Jan. 2009, 10(suppl 1.): S41, 10 pages.

Lee et al., "Identifying Potential Immunodominant Positions and Predicting Antigenic Variants of Influenza A/H3N2 Viruses", Vaccine, Nov. 2007, 25(48):8133-8139.

Nakaya et al., "Systems Biology of Vaccination for Seasonal Influenza in Humans", Nature Immunology, Jul. 2011, 12(8):786-795.

PCT International Search Report and Written Opinion in International Application No. PCT/US2020/056507, dated Feb. 5, 2021, 21 pages.

Qiu et al., "Computational Approaches and Challenges to Developing Universal Influenza Vaccines", Vaccines, May 2019, 7(2):45, 22 pages.

International Preliminary Report on Patentability in International Application No. PCT/US2020/056507, dated May 5, 2022, 14 pages.

Yao et al., "Predicting influenza antigenicity from Hemagglutintin sequence data based on a joint random forest method," Scientific Reports, May 8, 2017, 7(1):1545.

* cited by examiner

*Primary Examiner* — Olivia M. Wise
*Assistant Examiner* — Robert J. Kallal
(74) *Attorney, Agent, or Firm* — Fish & Richardson P.C.

(57) ABSTRACT

A system for designing vaccines includes one or more processors, and computer storage storing executable computer instructions in which, when executed by the one or more processers, cause the one or more processors to perform one or more operations. The one or more operations include applying, to a first temporal sequence data set, a plurality of driver models configured to generate output data representing one or more molecular sequences. The one or more operations include, for each of the plurality of driver models, training the driver model. The one or more operations include selecting, based on one or more trained translational responses, a set of trained driver models of the plurality of driver models. The one or more operations include selecting, based on second translational response data, a subset of trained driver models of the set of trained driver models.

19 Claims, 10 Drawing Sheets

| | Model | Antigens | Assays | Read-Out Panel | (Titers) Total Readouts |
|---|---|---|---|---|---|
| CYCLE 1 | Ferret | 90 H3N1 Virus | HAI/AF | 18 Strains (1950s-Present) | 3200 HAI / 3200 AF |
| | Mouse | 90 H3 rHA+AF03 | HAI/AF | 18 Strains (1950s-Present) | 1600 HAI/ 1600 AF |
| | MIMIC | 90 H3 rHA | HAI/AF | 18 Strains (1950s-Present) | 13000 SA-HAI/ 13000 AF |

| | Model | Antigens | Assays | Read-Out Panel | Total Readouts (Titers) |
|---|---|---|---|---|---|
| CYCLE 2 | Ferret | 9 H3N1 Virus | HAI/AF | 57 Strains (2009-Present) | 800 HAI / 1000 AF |
| | Mouse | 9 H3 rHA+AF03 | HAI/AF | 57 Strains (2009-Present) | 400 HAI/ 500 AF |
| | MIMIC | 9 H3 rHA | HAI/AF | 57 Strains (2009-Present) | 3200SA-HAI/ 4100 AF |

FIG. 8

SYSTEMS AND METHODS FOR DESIGNING VACCINES

CROSS-REFERENCE TO RELATED APPLICATIONS

This application claims priority to U.S. Provisional Patent Application Ser. No. 62/924,096, filed Oct. 21, 2019, the entire contents of this application is herein incorporated by reference.

TECHNICAL FIELD

This disclosure generally relates to systems and methods for generating vaccines.

BACKGROUND

The mammalian immune system uses two general mechanisms to protect the body against environmental pathogens. When a pathogen-derived molecule is encountered, the immune response becomes activated to ensure protection against that pathogenic organism.

The first immune system mechanism is the non-specific (or innate) inflammatory response. The innate immune system appears to recognize specific molecules that are present on pathogens but not on the body itself.

The second immune system mechanism is the specific or acquired (or adaptive) immune response. Innate responses are fundamentally the same for each injury or infection. In contrast, acquired responses arise specifically in response to molecules in the pathogen, or pathogen-derived molecules. The immune system recognizes and responds to structural differences between self and non-self (e.g. pathogen or pathogen-derived) proteins. Proteins that the immune system recognizes as non-self are referred to as antigens. Pathogens typically express large numbers of highly complex antigens. The acquired immune system leverages two facilities; first, the generation of immunoglobulins (antibodies) in response to many different molecules present in the pathogen, called antigens. The second recruits receptors to bind processed forms of the antigens that are presented on the surface of cells for identification as infected cells by others cells.

Taken together, acquired immunity is mediated by specialized immune cells called B and T lymphocytes (or simply B and T cells). Acquired immunity has specific memory for antigenic structures. Repeated exposure to the same antigen increases the response, which may increase the level of induced protection against that particular pathogen. B cells produce and mediate their functions through the actions of antibodies. B cell-dependent immune responses are referred to as "humoral immunity," because antibodies are found in body fluids. T cell-dependent immune responses are referred to as "cell mediated immunity," because effector activities are mediated directly by the local actions of effector T cells. The local actions of effector T cells are amplified through synergistic interactions between T cells and secondary effector cells, such as activated macrophages. The result is that the pathogen is killed and prevented from causing diseases.

Similar to pathogens, vaccines function by initiating an innate immune response at the vaccination site and activating antigen-specific T and B cells that can give rise to long term memory cells in secondary lymphoid tissues. The precise interactions of the vaccine with cells at the vaccination site and with T and B cells are important to the ultimate success of the vaccine.

In determining if a candidate antigen can be a functional and effective vaccine, the candidate antigen is typically required to undergo rigorous testing and evaluation protocols. Traditionally, a candidate antigen is tested pre-clinically by a process in which the candidate antigen is assessed by in vitro assays, ex vivo assays, and using various animal models (e.g., mouse models, ferret models, etc.).

An example type of assay that can be used to measure a biological response is a hemagglutination inhibition assay (HAI). An HAI applies the process of hemagglutination, in which sialic acid receptors on the surface of red blood cells (RBCs) bind to a hemagglutinin glycoprotein found on the surface of an influenza virus (and several other viruses) and create a network, or lattice structure, of interconnected RBC's and virus particles, referred to as hemagglutination, which occurs in a concentration dependent manner on the virus particles. This is a physical measurement taken as a proxy as to the facility of a virus to bind to similar sialic acid receptors on pathogen-targeted cells in the body. The introduction of anti-viral antibodies raised in a human or animal immune response to another virus (which may be genetically similar or different as the virus used to bind to the RBCs in the assay). These antibodies interfere with the virus-RBC interaction and change the concentration of virus sufficient to alter the concentration at which hemagglutination is observed in the assay. One goal of an HAI can be to characterize the concentration of antibodies in the antiserum or other samples containing antibodies relative to their ability to elicit hemagglutination in the assay. The highest dilution of antibody that prevents hemagglutination is called the HAI titer (i.e., the measured response).

Another approach to measuring biological responses is to measure a potentially larger set of antibodies elicited by a human or animal immune response, which are not necessarily capable of affecting hemagglutination in the HAI assay. A common approach for this leverages enzyme-linked immunosorbent assay (ELISA) techniques, in which a viral antigen (e.g. hemagglutinin) is immobilized to a solid surface, and then antibodies from the antisera are allowed to bind to the antigen. The readout measures the catalysis of a substrate of an exogenous enzyme complexed to either the antibodies from the antisera, or to other antibodies which themselves bind to the antibodies of the antisera. Catalysis of the substrate gives rise to easily detectable products. There are many variations of this sort of in vitro assay. One such variation is called antibody forensics (AF); which is a multiplexed bead array technique that allows a single sample of serum to be measured against many antigens simultaneously. These measurements characterize the concentration and total antibody recognition, as compared to HAI titers, which are taken to be more specifically related to interference with sialic acid binding by hemagglutinin molecules. Therefore, an antisera's antibodies may in some cases have proportionally higher or lower measurements than the corresponding HAI titer for one virus's hemagglutinin molecules relative to another virus's hemagglutinin molecules; in other words, these two measurements, AF and HAI, are not generally linearly related.

Currently, conventional candidate antigen testing may only be performed conditionally given the elicitation of preconceived "protective" immune responses. That is, if one animal or assay fails to demonstrate an appropriate response to the candidate antigen, the candidate antigen is usually "down-selected" (i.e., abandoned as a productive candidate). For example, an influenza antigen is often tested using a sequential selection protocol, where the antigen is first assessed by in vitro assays to ensure that the antigen is facile for large-scale production. Conditional on the antigen passing those requirements, the antigen is then assessed by immunization of, for example, mice to measure its ability to elicit a protective immune response from the mice. This response is usually expected to be protective to the antigen itself and to various other viral strains and/or viral strain components against which protection is desired. Ferrets may thereafter assessed in like manner, conditional on mice or other previous measurements having previously demonstrated what may be taken as suggestive of protective responses. Penultimate to assessment in humans, ex vivo platforms such as human immune system replicas or non-human primates may be assessed; again, conditionally on success in prior steps.

SUMMARY

In an aspect, a system for designing vaccines is provided. The system includes one or more processors. The system includes computer storage storing executable computer instructions in which, when executed by the one or more processers, cause the one or more processors to perform one or more operations. The one or more operations include applying, to a first temporal sequence data set, a plurality of driver models configured to generate output data representing one or more molecular sequences, the first temporal sequence data set indicating one or more molecular sequences and, for each of the one or more molecular sequences, one or more times of circulation for pathogenic strains including that molecular sequence as a natural antigen. The one or more operations include for each of the plurality of driver models, training the driver model by: i) receiving, from the driver model, output data representing one or more predicted molecular sequences based on the received first temporal sequence data set; ii) applying, to the output data representing the predicted one or more molecular sequences, a translational model configured to predict a biological response to molecular sequences for a plurality of translational axes to generate first translational response data representing one or more first translational responses corresponding to a particular translational axis of the plurality of translational axes based on the one or more predicted molecular sequences of the output data; iii) adjusting one or more parameters of the driver model based on the first translational response data; and iv) repeating steps i-iii for a number of iterations to generate trained translational response data representing one or more trained translational responses corresponding to the particular translational axis. The one or more operations include selecting, based on the one or more trained translational responses, a set of trained driver models of the plurality of driver models. The one or more operations include for each trained driver model of the set of trained driver models: applying, to a second temporal sequence data set, the trained driver model to generate trained output data representing one or more predicted molecular sequences for a particular season; applying, to the final output data, the translational model to generate second translational response data representing, for each translational axis of the plurality of translational axes, one or more second translational responses; and selecting, based on the second translational response data, a subset of trained driver models of the set of trained driver models.

At least one of the plurality of driver models can include a recurrent neural network. At least one of the plurality of driver models includes a long short-term memory recurrent neural network.

The output data representing one or more predicted molecular sequences based on the received first temporal sequence data set can include output data representing an antigen for each of a plurality of pathogenic seasons. The output data representing an antigen for each of a plurality of pathogenic seasons can include an antigen determined by predicting molecular sequences that will generate a maximized aggregate biological response across all pathogenic strains in circulation for a particular season. The output data representing an antigen for each of a plurality of pathogenic seasons can include an antigen determined by predicting molecular sequences that will generate a response that will effectively immunize against a maximized number of viruses in circulation for a particular season.

The plurality of translational axes can include at least one of a: ferret antibody forensics (AF) axis, ferret hemagglutination inhibition assay (HAI) axis, mouse AF axis, mouse HAI axis, human Replica AF axis, human AF axis, or human HAI axis. The number of iterations can be based on a predetermined number of iterations. The number of iterations can be based on a predetermined error value. The one or more first translational responses can include at least one of: a predicted ferret HAI titer, a predicted ferret AF titer, a predicted mouse AF titer, a predicted mouse HAI titer, a predicted human replica AF titer, a predicted human AF titer, or a predicted human HAI titer.

Selecting the set of trained driver models of the plurality of driver models can include assigning each driver model of the plurality of driver models to a class of driver models, wherein each class is associated with the particular translational axis of the plurality of translational axes used to train that driver model. Selecting the set of trained driver models of the plurality of driver models can include comparing, for each driver model of the plurality of driver models, the one or more trained translational responses of that driver model with the one or more trained translational responses of at least one other driver model assigned to the same class as that driver model.

The operations can further include for each trained driver model of the subset of trained driver models: validating that trained driver model by comparing the second translational response data corresponding to that trained driver model with observed experimental response data; and generating, in response to validating that trained driver model, a vaccine that includes the one or more molecular sequences represented by the trained output data corresponding to that trained driver model.

In an aspect, a system is provided. The system includes a computer-readable memory comprising computer-executable instructions. The system includes at least one processor configured to execute executable logic including at least one machine learning model trained to predict one or more molecular sequences, in which when the at least one processor is executing the computer-executable instructions, the at least one processor is configured to carry out one or more operations. The one or more operations include receiving temporal sequence data indicating one or more molecular sequences and, for each of the one or more molecular sequences, one or more times of circulation for pathogenic strains including that molecular sequence as a natural antigen. The one or more operations include processing the temporal sequence data through one or more data structures storing one or more portions of executable logic included in the machine learning model to predict one or more molecular sequences based on the temporal sequence data.

Predicting one or more molecular sequences based on the temporal sequence data can include predicting one or more immunological properties the predicted one or more molecular sequences will confer for use at a future time. Predicting the one or more molecular sequences based on the temporal sequence data can include predicting one or more molecular sequences that will generate a maximized aggregate biological response across all pathogenic strains of the temporal sequence data. Predicting the one or more molecular sequences based on the temporal sequence data can include predicting one or more molecular sequences that will generate a biological response that will effectively cover a maximized number of pathogenic strains of the temporal sequence data. The predicted one or more molecular sequences can be used to design a vaccine for pathogenic strains circulating during a time subsequent to the one or more times of circulation of the temporal sequence data.

The machine learning model can include a recurrent neural network.

These and other aspects, features, and implementations can be expressed as methods, apparatus, systems, components, program products, methods of doing business, means or steps for performing a function, and in other ways, and will become apparent from the following descriptions, including the claims.

Implementations of the present disclosure can provide one or more of the following advantages. When compared with traditional techniques, vaccines can be designed for a future pathogenic season to confer more protection in terms of an amount of biological response for at least one pathogenic strain of that future pathogenic season. When compared with traditional techniques, vaccines can be designed for future pathogenic seasons to confer more protection in terms of breadth of effective coverage for a plurality of pathogenic strains of that future pathogenic season (that is, elicit an effective immunological response for a number of pathogenic strains in a future pathogenic season). Unlike traditional techniques, rarely observed strains that may confer "more protection" because they cross-react with more strains than frequently observed strains can be assessed and their vaccination effectiveness can be predicted.

These and other aspects, features, and implementations can be expressed as methods, apparatus, systems, components, program products, means or steps for performing a function, and in other ways.

These and other aspects, features, and implementations will become apparent from the following descriptions, including the claims.

BRIEF DESCRIPTION OF THE DRAWINGS

FIG. 8 shows an example of data used to train a machine learning model for predicting biological responses.

DETAILED DESCRIPTION

Figure 1:
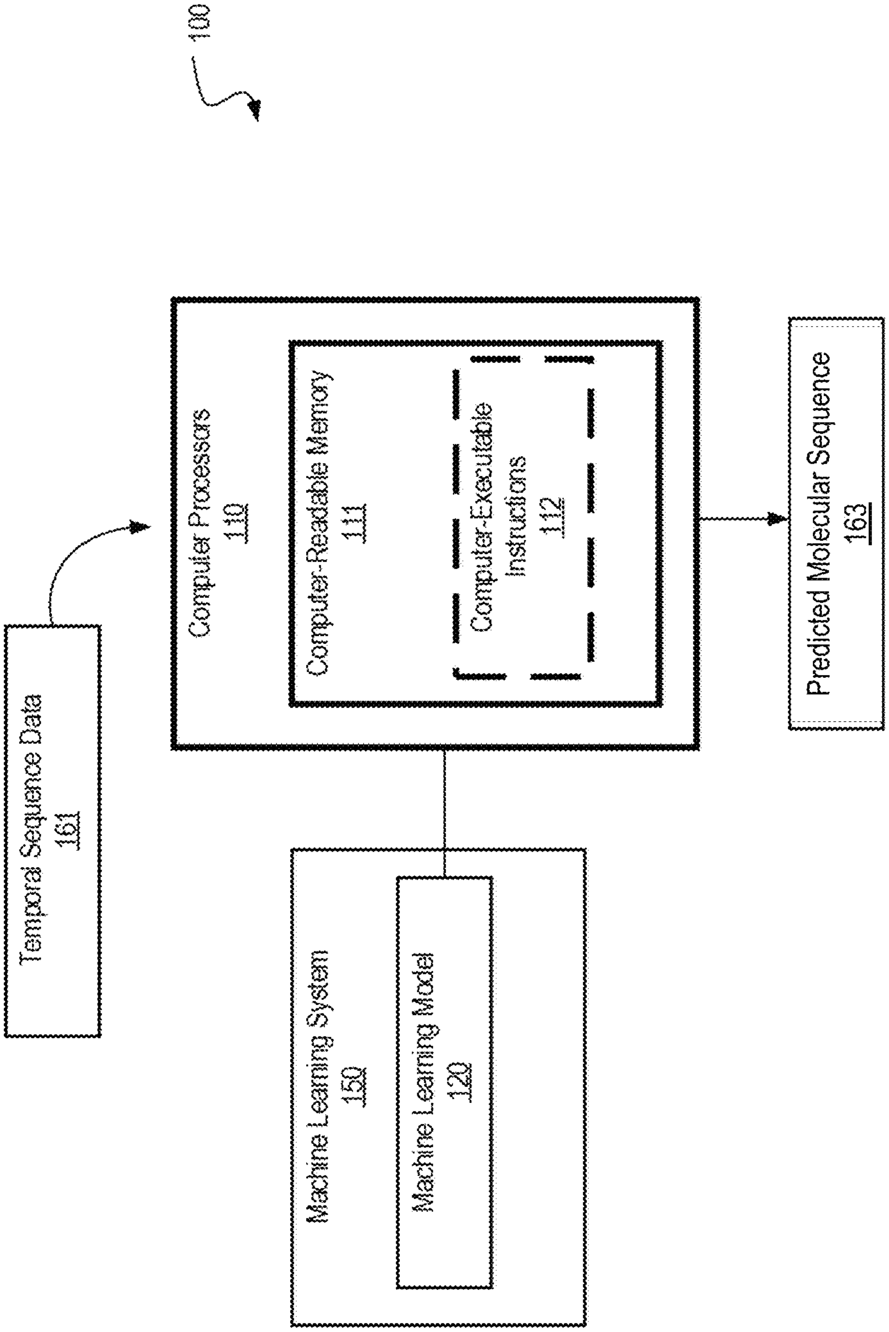
FIG. 1 shows an example of a system for designing vaccines.

Traditional methods of choosing a candidate vaccine (CV), and/or its antigens expressed as recombinant proteins, may generally rely on several assumptions. As an illustrative example, in the case of influenza, traditional methods of choosing a CV may assume the following: (1) that, for any given pathogenic season, there is a "dominant strain"; (2) naive ferrets are an accurate model of influenza drift (that is, cross-reactivity in ferrets demonstrates whether one CV, as an antigen, would confer protection against other circulating influenza strains; and (3) gains in ferret cross-reactivity can be a reliable predictor of gains in human vaccine efficacy. Based on these assumptions, traditional methods of choosing a CV may have the following solutions: (1) choose a CV that protects against the dominant strain; (2) establish a correlate of protection using, for example, ferret HAI; and (3) asses cross-reactivity of clinical isolates in ferrets. Furthermore, traditional methods of choosing a CV typically involve selecting CVs that were prevalent in the year preceding the year for vaccine recommendation and assessing (typically using ferrets) the selected CVs against other frequently observed pathogenic strains.

While these assumptions may have facilitated effective CVV selection 50 or more years ago, when 1-10 pathogenic isolates were observed in a year, these assumptions may not facilitate effective CVV selection in current pathogenic seasons, in which thousands of pathogenic isolates may be observed and reported. This is because it may be difficult to scale ferret assessments to thousands of pathogenic isolates. Potentially, as a result, current selections of seasonal influenza vaccines, for example, typically achieve less than 50% vaccine effectiveness (that is, percentage reduction of severe disease in case-seeking individual between a vaccinated group of people as compared to an unvaccinated group).

The systems and methods described in this specification can be used to alleviate one or more of the aforementioned disadvantages of traditional CV selection techniques. According to the systems and methods described in this disclosure, a subset of an initial plurality of machine learning models (which may be referred to as driver models in this specification) are used to select one or more molecular sequences (for example, antigenic sequences) that are predicted to excel in at least one translational axis. A translational axis can refer to a measure of biological response of a human or non-human model to, for example, an antigen (for example, a resulting HAI titer of a mouse exposed to a particular antigen or a resulting HAI titer of collected human sera). The subset of driver models can be chosen for use in a rational manner by first assigning each driver model of the initial plurality of driver models to a class of translational axis, in which each class of translational axis corresponds to a translational axis of a plurality of translational axes (for example, at least one of: ferret AF, ferret HAI, mouse AF, mouse HAI, human replica AF, human AF, or human HAI).

In some implementations, each driver model is trained to predict molecular sequences that will generate an extremal (for example, maximized) biological response (for example, a maximized mouse HAI titer) across all pathogenic strains in circulation for a particular pathogenic season, or will generate a response that will effectively cover a maximized number of pathogenic strains in circulation for a particular pathogenic season, based on temporal sequence data representing a plurality of molecular sequences and, for each molecular sequence, times of circulation for pathogenic strains including that molecular sequence as a natural antigen. In some implementations, for each driver model, a translational model configured to predict a biological response to molecular sequences for the plurality of translational axes is used to provide feedback in the form of translational response data representing one or more translational responses corresponding to the translational axis class assigned to that driver model.

This process is performed over a number of iterations in which, for each iteration, the driver model updates one or more parameters (which are often referred to as weights and biases) based on the feedback from the translational model. After the number of iterations, a set of trained driver models are selected. The selected set of trained driver models can include, for each class of translational axis, the trained driver model that predicted a molecular sequence resulting in a desired (often: highest) aggregate (for example, averaged) biological response (for example, immunological response) as predicted by the translational model for that class of translational axis. For each trained driver model of the set of trained driver models, the antigen predicted by that trained driver model can then be applied to the translational model, which predicts a response to that antigen for each translational axis.

A subset of trained driver models of the set of trained driver models is then selected. Selecting the subset of trained driver models can include selecting, for each translational axis, the trained driver model of the set of trained driver models that predicted the antigen eliciting the highest aggregate biological response across all pathogenic strains for a particular pathogenic season as predicted by the translational model for that translational axis. Each trained driver model of the subset of trained driver models is validated using observed data from human or non-human experiments. If the trained driver model is validated, it can be used to design a vaccine based on the antigen predicted by the validated trained driver model.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all implementations or that the features represented by such element may not be included in or combined with other elements in some implementations.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Several features are described hereafter that can each be used independently of one another or with any combination of other features. However, any individual feature may not address any of the problems discussed above or might only address one of the problems discussed above. Some of the problems discussed above might not be fully addressed by any of the features described herein. Although headings may be provided, data related to a particular heading, but not found in the section having that heading, may also be found elsewhere in this description.

FIG. 1 shows an example of a system 100 for designing vaccines. The system 100 includes computer processors 110. The computer processors 110 include computer-readable memory 111 and computer readable instructions 112. The system 100 also includes a machine learning system 150. The machine learning system 150 includes a machine learning Model 120. The machine learning system 150 may be separate from or integrated with the computer processors 110.

The computer-readable memory 111 (or computer-readable medium) can include any data storage technology type which is suitable to the local technical environment, including, but not limited to, semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In an implementation, the computer-readable memory 111 includes code-segment having executable instructions.

In some implementations, the computer processors 110 include a general purpose processor. In some implementations, the computer processors 110 include a central processing unit (CPU). In some implementations, the computer processors 110 include at least one application specific integrated circuit (ASIC). The computer processors 110 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 110 are configured to execute program code means such as the computer-executable instructions 112. In some implementations, the computer processors 110 are configured to execute the machine learning model 120.

The computer processors 110 are configured to receive a temporal sequence data set 161. The temporal sequence data set 161 can include data representing one or more molecular sequences and, for each of the one or more molecular sequences, one or more times of circulation for pathogenic strains including that molecular sequence as a natural antigen. As an illustrative example, the temporal sequence data set 161 can indicate molecular sequences and times of circulation (for example, specific months, specific pathogenic season, and so forth) for A/SINGAPORE/INFIMH160019/2016, A/MISSOURI/37/2017, A/KENYA/105/2017, A/MIYAZAKI/89/2017, A/ETHIOPIA/1877/201, A/OSORNO/60580/2017, A/BRISBANE/1059/2017, and A/VICTORIA/11/2017. Although only 8 pathogenic strains are described, the temporal sequence data set 161 can include molecular sequence information and times of circulation corresponding to billions of pathogenic strains. The temporal sequence data set 161 can be obtained through one or more means, such as wired or wireless communications with databases (including cloud-based environments), optical fiber communications, Universal Serial Bus (USB), compact disc read-only memory (CD-ROM), and so forth.

The machine learning system 150 applies machine learning techniques to train the machine learning model 120 that, when applied to the input data, generates indications of whether the input data items have the associated property or properties, such as probabilities that the input data items have a particular Boolean property, an estimated value of a scalar property, or an estimated value of a vector (i.e., ordered combination of multiple scalars).

As part of the training of the machine learning model 120, the machine learning system 150 can form a training set of input data by identifying a positive training set of input data items that have been determined to have the property in question, and, in some implementations, forms a negative training set of input data items that lack the property in question.

The machine learning system 150 extracts feature values from the input data of the training set, the features being variables deemed potentially relevant to whether or not the input data items have the associated property or properties. An ordered list of the features for the input data is herein referred to as the feature vector for the input data. In some implementations, the machine learning system 150 applies dimensionality reduction (e.g., via linear discriminant analysis (LDA), principle component analysis (PCA), learned deep features from a neural network, or the like) to reduce the amount of data in the feature vectors for the input data to a smaller, more representative set of data.

In some implementations, the machine learning system 150 uses supervised machine learning to train the machine learning model 120 with the feature vectors of the positive training set and the negative training set serving as the inputs. Different machine learning techniques—such as linear support vector machine (linear SVM), boosting for other algorithms (e.g., AdaBoost), neural networks, logistic regression, naïve Bayes, memory-based learning, random forests, bagged trees, decision trees, boosted trees, or boosted stumps—are used in some implementations. The machine learning model 120, when applied to the feature vector extracted from the input data item, outputs an indication of whether the input data item has the property in question, such as a Boolean yes/no estimate, a scalar value representing a probability, a vector of scalar values representing multiple properties, or a nonparametric distribution of scalar values representing different ad no a priori fixed numbers of multiple properties, which may be represented either explicitly or implicitly in a Hilbert or similar infinite dimensional space.

In some implementations, a validation set is formed of additional input data, other than those in the training sets, which have already been determined to have or to lack the property in question. The machine learning system 150 applies the trained machine learning model 120 to the data of the validation set to quantify the accuracy of the machine learning model 120. Common metrics applied in accuracy measurement include: Precision=TP/(TP+FP) and Recall=TP/(TP+FN), where precision is how many the machine learning model 120 correctly predicted (TP or true positives) out of the total it predicted (TP+FP or false positives), and recall is how many the machine learning model 120 correctly predicted (TP) out of the total number of input data items that did have the property in question (TP+FN or false negatives). The F score (F score=2*PR/(P+R)) unifies precision and recall into a single measure. In some implementations, the machine learning system 150 iteratively re-trains the machine learning model 120 until the occurrence of a stopping condition, such as the accuracy measurement indication that the model 120 is sufficiently accurate, or a number of training rounds having taken place.

In some implementations, the machine learning model 120 includes a neural network. In some implementations, the neural network includes a recurrent neural network RNN. A RNN generally describes a class of artificial neural networks where connections between nodes form a directed graph along a temporal sequence, which allows it to exhibit temporal dynamic behavior. Unlike feedforward neural networks, RNNs can use their internal state (memory) to process sequences of inputs. In some implementations, the RNN includes a long short-term memory (LSTM) architecture. LSTM refers to an RNN architecture that has feedback connections and can process, not only process single data points (such as images), but also entire sequences of data (such as speech or video). The machine learning model 120 can include other types of neural networks, such as convolutional neural networks, radial basis function neural networks, physical neural networks (for example, optical neural networks), and so forth. Example methods of designing and training the machine learning model 120 are discussed later in more detail with reference to FIGS. 2A-4.

The machine learning model 120 is configured to predict, based on the received temporal sequence data set 161, one or more molecular sequences and what immunological properties the predicted one or more molecular sequences will confer for use at a future time. As an illustrative example, assume that the received temporal sequence data set 161 included data representing a plurality of pathogenic strains, in which each pathogenic strain was found to be in circulation at one or more times between Jan. 1, 2014 and Dec. 31, 2018. The machine learning model 120 can predict one or more molecular sequences (for example, antigens) that will generate a maximized aggregate biological response (for example, a maximized average human HAI titer) across all viruses in circulation between Jan. 1, 2019 and May 31, 2019 based on the pathogenic strains found to be in circulation at one or more times between Jan. 1, 2014 and Dec. 31, 2018. Additionally or alternatively, the machine learning model 120 can predict one or more molecular sequences that will generate a biological response that will effectively cover (for example, effectively vaccinate against) a maximized number of viruses in circulation between Jan. 1, 2019 and May 31, 2019 based on the pathogenic strains found to be in circulation at one or more times between Jan. 1, 2014 and Dec. 31, 2018. The predicted one or more molecular sequences can be used to design a vaccine for the viruses circulating during the future time (such as Jan. 1, 2019 through May 31, 2019 of the previous example).

Figure 2A:
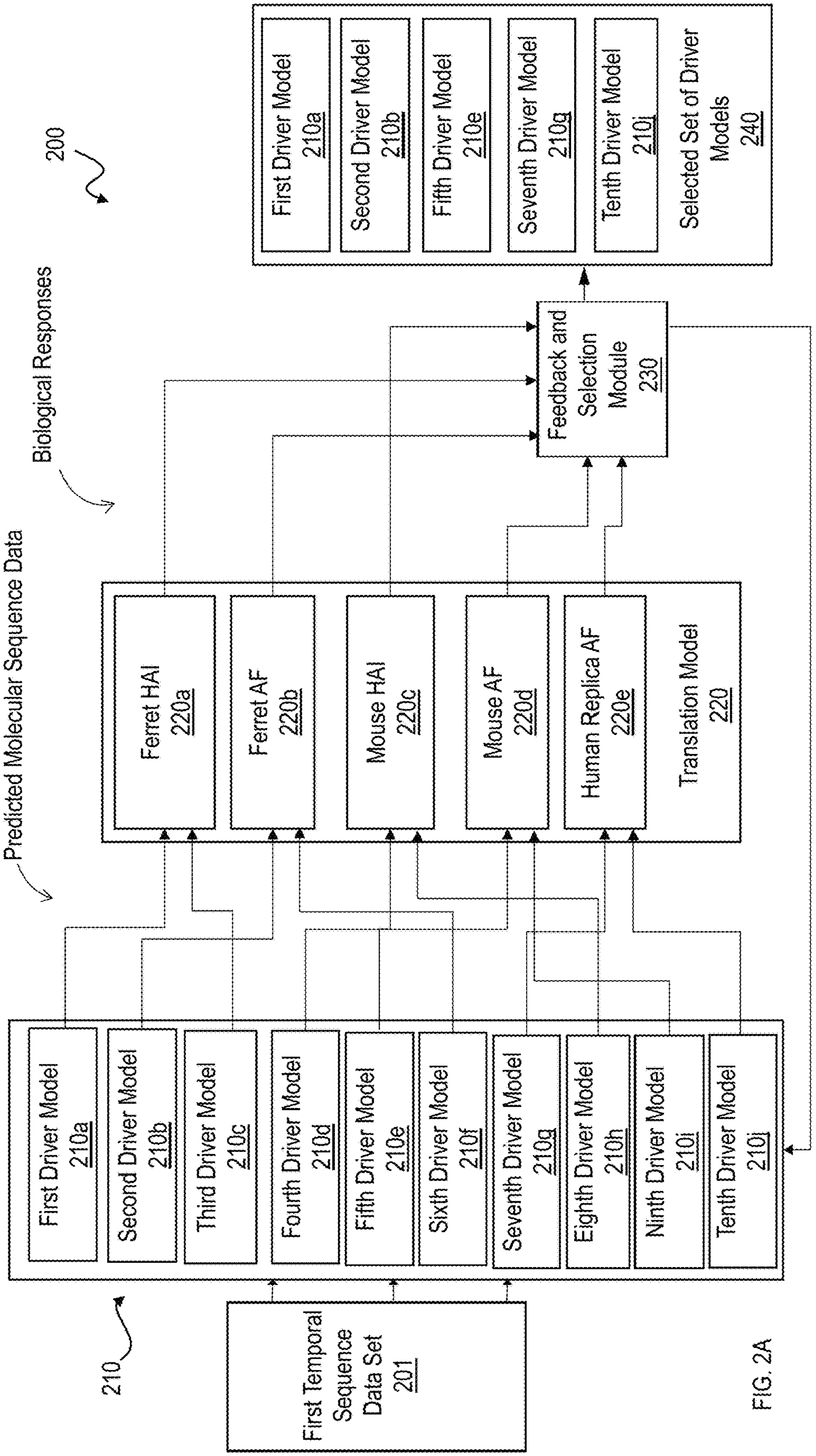
FIGS. 2A-2B show a flow diagram of a method for designing a system for designing vaccines.
Figure 2B:
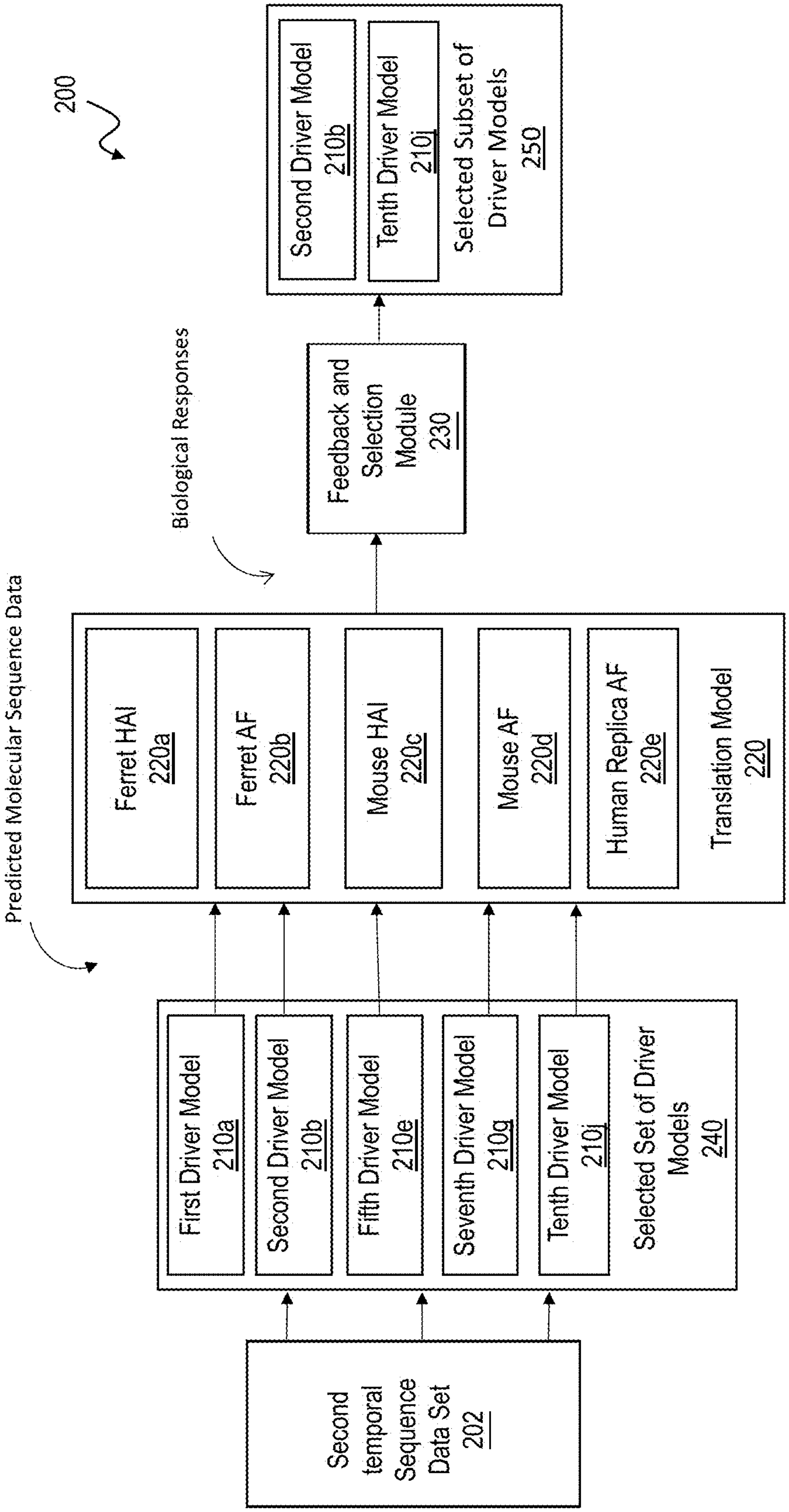

FIGS. 2A-2B shows a flow diagram of an architecture 200 for designing a system for designing vaccines. The architecture 200 includes a plurality of driver models 210, a translational model 220, and a feedback and selection module 230. First, a plurality of driver models 210 are initiated. Each of the plurality of driver models 210 are configured to generate data representing one or more molecular sequences (for example, antigens) and predictions as to what immunological property each of the molecular sequences will confer for use, as discussed previously with reference to the machine learning model 120 of FIG. 1. In the shown implementation, the plurality of driver models 210 include a first driver model 210*a*, a second driver model 210*b*, a third driver model 210*c*, a fourth driver model 210*d*, a fifth driver model 210*e*, a sixth driver model 210*f*, a seventh driver model 210*g*, an eighth driver model 210*h*, a ninth driver model 210*i*, and a tenth driver model 210*j*. While ten driver models are shown, the plurality of driver models 210 can include more or fewer driver models (for example, 5 driver models, 30 driver models, 100 driver models, and so forth). One or more of the driver models can be, for example, an RNN as described earlier with reference to FIG. 1.

The translational model 220 is configured to predict a biological response to molecular sequences for a plurality of translational axes. In the shown implementation, the translational model 220 includes a ferret HAI translational axis 220*a*, a ferret AF translational axis 220*b*, a mouse HAI axis 220*c*, a mouse AF translational axis 220*d*, and a human replica AF translational axis 220*e*. While specific translational axes are shown, implementations are not limited to those specific translational axes. For example, the translational model can additionally, or alternatively, include a human HAI translational axis, a human AF translational axis, a human replica HAI axis, or a combination of them, among others. Some implementations of the translational model 220 are discussed later in more detail with reference to FIGS. 6-9.

Referring to FIG. 2A, each of the driver models of the plurality of driver models 210 are assigned to a specific translational axis of the translational model 220. In the shown implementation, the first driver model 210*a* and the third driver model 210*c* are assigned to the ferret HAI translational axis 220*a*, the second driver model 210*b*, and the sixth driver model 210*f* are assigned to the ferret AF translational axis 220*b*, the fourth driver model 210*d* and the eighth driver model 210*h* are assigned to the mouse HAI translational axis 220*c*, the fifth driver model 210*e* and the ninth driver model 210*i* are assigned to the mouse AF translational axis 220*d*, and the seventh driver model 210*g* and the tenth driver model 210*j* are assigned to the human replica AF translational axis 220*e*.

Each driver model of the plurality of driver models 210 receive a first temporal sequence data set 201. The first temporal sequence data set 201 can include a plurality of molecular sequences and times of circulation for pathogenic strains containing at least one of the plurality of molecular sequences as a natural antigen. As an illustrative example, the first temporal sequence data set 201 can include molecular sequence and circulation times for all observed pathogenic strains that were in circulation at times between Jan. 1, 2014 and Dec. 31, 2018 (which may be referred to as the "pathogenic time period"). Based on the received first temporal sequence data set 201, each driver model of the plurality of driver models 220 is capable of generating output data representing one or more molecular sequences. For example, the output data can represent a molecular sequence (such as an antigen) for each pathogenic season of the pathogenic time period. For each pathogenic season, the molecular sequence can be determined by predicting a molecular sequence that will generate a maximized aggregate biological response across all viruses in circulation for that pathogenic season, and/or will generate a response that will effectively cover (for example, effectively vaccinate against) a maximized number of viruses in circulation for that pathogenic season, based on the temporal strain data from one or more pathogenic seasons preceding that pathogenic season.

The translational model 220 is capable of receiving the output data from each driver model of the plurality of driver models 210 and generating, for each driver model of the plurality of driver models 210, first translational response data representing one or more translational responses corresponding to the particular translational axis assigned to that driver model. In the shown example, the translational model 220 can receive, from the first driver model 210*a*, the output data representing the predicted one or more molecular sequences, and predict a ferret HAI titer for each molecular sequence of the one or more molecular sequences across all pathogenic strains in circulation for each pathogenic season according to the ferret HAI translational axis 220*a* (that is, for each pathogenic strain of a particular pathogenic season, predict an immunological response of a ferret being exposed to that pathogenic strain after being immunized by the predicted molecular sequence).

The first translational response data corresponding to each driver model of the plurality of driver models 210 is received by the feedback and selection module 230, which compares the predicted response for each pathogenic season to a threshold response. For example, the feedback and selection module 230 can, for each driver model, aggregate (for example, average) the predicted biological responses across all viruses of each pathogenic season, compare that aggregate response to a threshold aggregate response, and generate an error value based on the comparison. Additionally, or alternatively, the feedback and selection module 230 can, for each driver model, compare the number of viruses effectively vaccinated against for each pathogenic season to a threshold number, and generate an error value based on that comparison. The feedback and selection module 230 can then cause each driver model to adjust one or more parameters (such as, their weights and biases) based on the error values for each pathogenic season. This process is repeated for a number of iterations. The number of iterations can be a set number of iterations or determined based on a threshold error value (that is, the process will continue until the threshold error value is exceeded). Thus, at a high level: (1) each driver model can predict, for a particular pathogenic season of the pathogenic time period, one or more molecular sequences to be used to immunize against pathogenic strains of that particular pathogenic season based on pathogenic strains of preceding pathogenic seasons; (2) the performance of each driver model can be assessed for each pathogenic season; and (3) the parameters of each driver model can be adjusted based on its performance in each pathogenic season.

After the number of iterations, the performance of each of the driver models (which may now be referred to as trained driver models) is compared with the other driver models assigned to the same translational axis as that driver model, and the driver model exhibiting the best performance is selected to generate a selected set of trained driver models 240. For example, after the number of iterations, the aggregate predicted ferret HAI titers for the molecular sequences predicted by the first driver model 210*a* can be compared with the aggregate predicted ferret HAI titers for the molecular sequences predicted by the third driver model, and the feedback and selection module 230 can select the driver model corresponding to the highest aggregate predicted ferret HAI titers (or the highest number of pathogenic strains effectively vaccinated against) across all or some of the pathogenic seasons of the pathogenic time period. In the shown implementation, the selected set of driver models 240 includes the first driver model 210*a*, the second driver model 210*b*, the fifth driver model 210*e*, the seventh driver model 210*g*, and the tenth driver model 210*j*.

Referring to FIG. 2B, each of the selected set of driver models 240 receives a second temporal sequence data set 202 and generates, based on the second temporal sequence data set 202, trained output data representing one or more molecular sequences for a particular pathogenic season. Similar to the first temporal sequence data set 201, the second temporal sequence data set 202 can include data representing molecular sequence and circulation times for all observed pathogenic strains that were in circulation for a given pathogenic time period. The pathogenic time period of the second temporal sequence data set 202 can be the same as, or different than, the pathogenic time period of the first temporal sequence data set 201. Each of the driver models of the selected set of driver models 240 are capable of predicting one or more molecular sequences (for example, antigens) for one or more pathogenic seasons. In some implementations, the predicted one or more molecular sequences are for one of the pathogenic seasons of the temporal time period (for example, the latest pathogenic season). As an illustrative example, assume that the received second temporal sequence data set 202 includes data representing a plurality of pathogenic strains in which each pathogenic strain was found to be in circulation at one or more times between Jan. 1, 2014 and Apr. 31, 2018. Each of the driver models of the selected set of driver models 240 can predict one or more molecular sequences (for example, an antigen) that will either generate a maximized aggregate biological response across all viruses in circulation between Oct. 1, 2017 and Apr. 31, 2019 based on the pathogenic strains found to be circulating in preceding pathogenic seasons between Jan. 1, 2014 and Sep. 30, 2017. Additionally or alternatively, each of the driver models of the selected set of driver models 240 can predict one or more molecular sequences that will generate a biological response that will effectively cover (for example, effectively vaccinate against) a maximized number of viruses in circulation between Oct. 1, 2017 and Apr. 31, 2018 based on the pathogenic strains found to be circulating in preceding pathogenic seasons between Jan. 1, 2014 and Sep. 30, 2017.

The translational model 220 receives the trained output data from each of the driver models of the selected set of driver models 240 and generates, based on the trained output data, second translational response data for each of the driver models. The second translational response data represents, for each driver model, one or more translational responses across all translational axes of the translational model 220 based on the predicted one or more molecular sequences of that driver model. As an illustrative example, the translational model 220 can receive trained output data from the first driver model 210*a* representing one or more molecular sequences. The translational model 220 can predict a ferret HAI titer, a ferret AF titer, a mouse HAI titer, a mouse AF titer, and a human replica AF titer for the one or more molecular sequences predicted by the first driver model 210*a* across all strains. The second translational response data for each driver model of the selected set of driver models 240 is received by the feedback and selection module 230. The feedback and selection module 230 is capable of comparing the performances of each driver model for each translational axis, and selecting the highest performing driver model in each axis, or combination of axes, to generate a selected subset of driver models 250. Using the previous illustrative example, regarding the ferret HAI axis 220*a*, the feedback and selection module 230 can compare the aggregate HAI titer across all pathogenic strains circulating between Jan. 1, 2019 and May 31, 2019 for the one or more molecular sequences predicted by each of the driver models of the selected set of driver models 240. The feedback and selection module 230 can then select the driver model found to have the highest aggregate HAI titer across all the pathogenic strains. In the shown implementation, the selected subset of driver models 250 includes the second driver model 210*b* and the tenth driver model 210*j*. One or more of the selected subset of driver models 250 can be included in the machine learning model 120 discussed previously with reference to FIG. 1.

Each of the driver models of the selected subset of driver models 250 can then be validated based on observations from real world experiments. For example, the second translational response data corresponding to the second driver model 210*b* can be compared with biological responses observed in human HAI experiments (or ferret HAI experiments, mouse HAI experiments, and so forth) in which human subjects are vaccinated with the one or more molecular sequences predicted by the second driver 210*b* and exposed to one or more of the pathogenic strains in circulation between Oct. 1, 2017 and Apr. 31, 2018. The predicted response and the observed response can be compared by the feedback and selection module 230 to generate an error value, and the feedback and selection module 230 can determine if one or more of the translational axes corresponding the second driver model 210*b* (for example, the ferret HAI translational axis 220*a* if the second driver model 210*b* was selected based on its performance in the ferret HAI translational axis 220*a*) is a good or bad predictor of human responses based on the error value. If the error value satisfies an error value threshold, the one or more molecular sequences predicted by the second driver model 210*b* can be used to design a vaccine for at least the Oct. 1, 2017 and Apr. 31, 2018 pathogenic season, or even pathogenic seasons following that pathogenic season. If, for example, a real-world ferret HAI experiment was used to validate the second driver model 210*b*, the determined error value can be used to adjust the parameters of the translational model 220, the second driver model 210*b*, or both.

Figure 3:
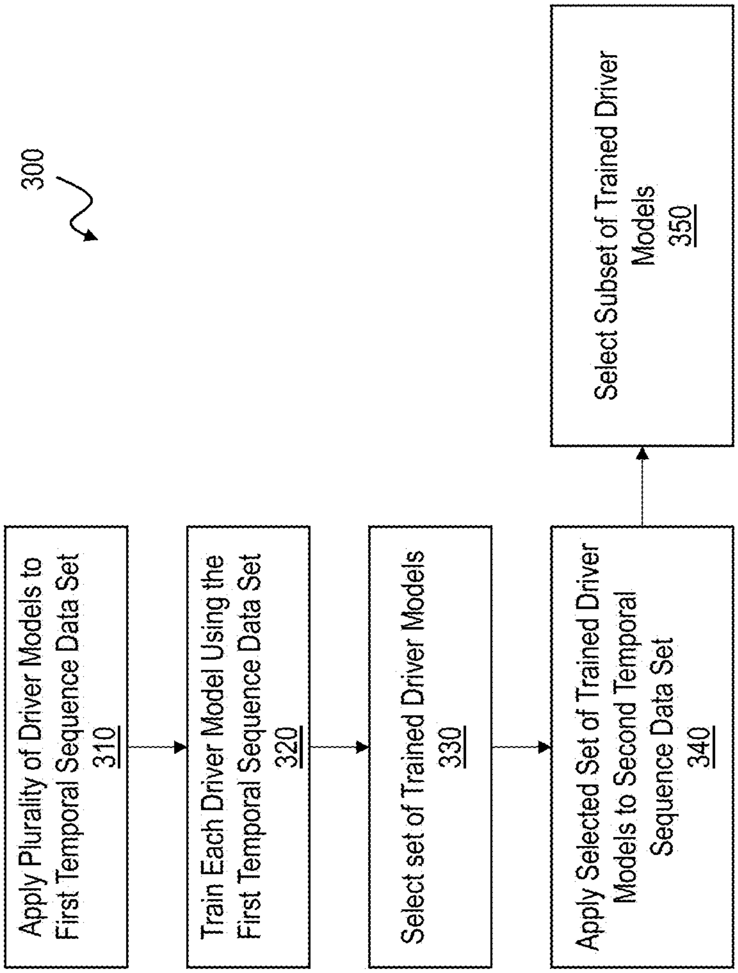
FIG. 3 shows a flowchart of a method for designing vaccines

FIG. 3 shows a flowchart of a method 300 for designing vaccines. For illustrative purposes, the method 300 will be described as being performed by the architecture 200 described earlier with reference to FIGS. 2A-2B. The method includes applying a plurality of driver models to a first temporal sequence data set (block 310), training each driver model using the first temporal sequence data set (block 320), selecting a set of trained driver models (block 330), applying the selected set of trained driver models to a second temporal sequence data set (block 340) and selecting a subset of trained driver models (block 350).

At block 310 each driver model of the plurality of driver models 210 receive a first temporal sequence data set 201. Based on the received first temporal sequence data set 201, each driver model of the plurality of driver models 220 can generate output data representing one or more molecular sequences.

Figure 4:
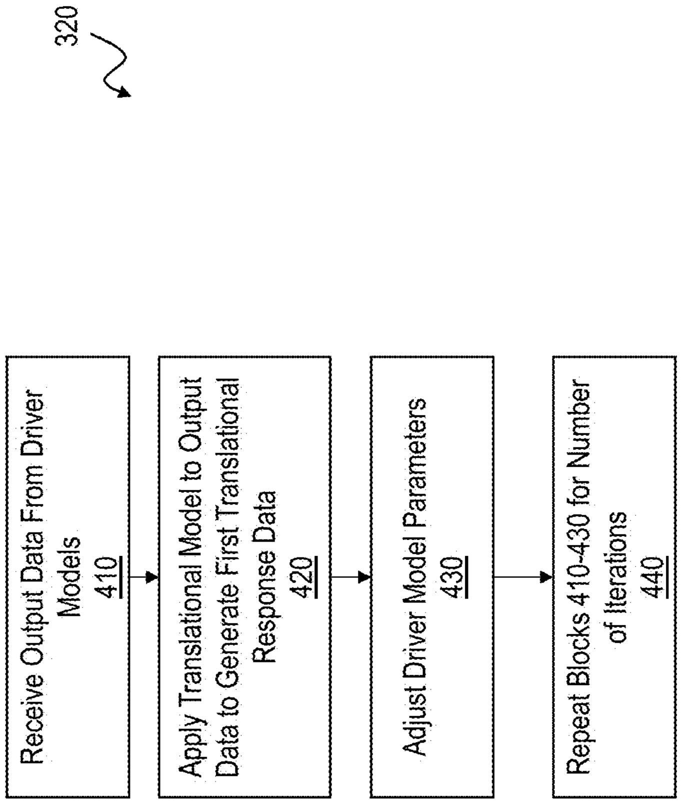
FIG. 4 shows a flowchart of a method for training one or more driver models for designing vaccines.

At block 320, for each of the driver models 210, that driver model is trained using a translational axis of the translational model 220 assigned to that driver model. FIG. 4 shows a flowchart of a method 400 for training one or more driver models for designing vaccines. Referring to FIG. 4, the method 400 includes receiving output data from each of the driver models of the plurality of driver models 210 (block 410), applying the translational model 220 to the output data to generate first translational response data for each of the driver models of the plurality of driver models 210 according to the translational axis assigned to that driver model (block 420), adjusting, for each driver model of the plurality of driver models 210, one or more parameters of that driver model based on the first translational response data corresponding to that driver model (block 430), and repeating block 410-430 for a number of iterations (block 440).

At block 330, a selected set of driver models 240 is generated based on, for each translational axis of the translational model 220, the performance of the driver models assigned to that translational axis. For example, after the number of iterations, the aggregate predicted ferret HAI titers for the molecular sequences predicted by the first driver model 210*a* can be compared with the aggregate predicted ferret HAI titers for the molecular sequences predicted by the third driver model 210*c*, and the feedback and selection module 230 can select the driver model corresponding to the highest aggregate predicted ferret HAI titers (or the highest number of pathogenic strains effectively vaccinated against).

At block 340, each of the selected set of driver models 240 receives a second temporal sequence data set 202 and generates, based on the second temporal data sect 202, trained output data representing one or more molecular sequences for a particular pathogenic season.

At block 350, the translational model 220 receives the trained output data from each of the driver models of the selected set of driver models 240 and generates, based on the trained output data, second translational response data for each of the driver models. The second translational response data represents, for each driver model, one or more translational responses across all translational axes of the translational model 220 based on the predicted one or more molecular sequences of that driver model. As an illustrative example, the translational model 220 can receive trained output data from the first driver model 210*a* representing one or more molecular sequences. The translational model 220 can predict a ferret HAI titer, a ferret AF titer, a mouse HAI titer, a mouse AF titer, and a human replica AF titer for the one or more molecular sequences predicted by the first driver model 210*a*. The second translational response data for each driver model of the selected set of driver models 240 is received by the feedback and selection module 230. The feedback and selection module 230 is capable of comparing the performances of each driver model for each translational axis, and selecting the highest performing driver model in each axis to generate a selected subset of driver models 250.

Figure 5:
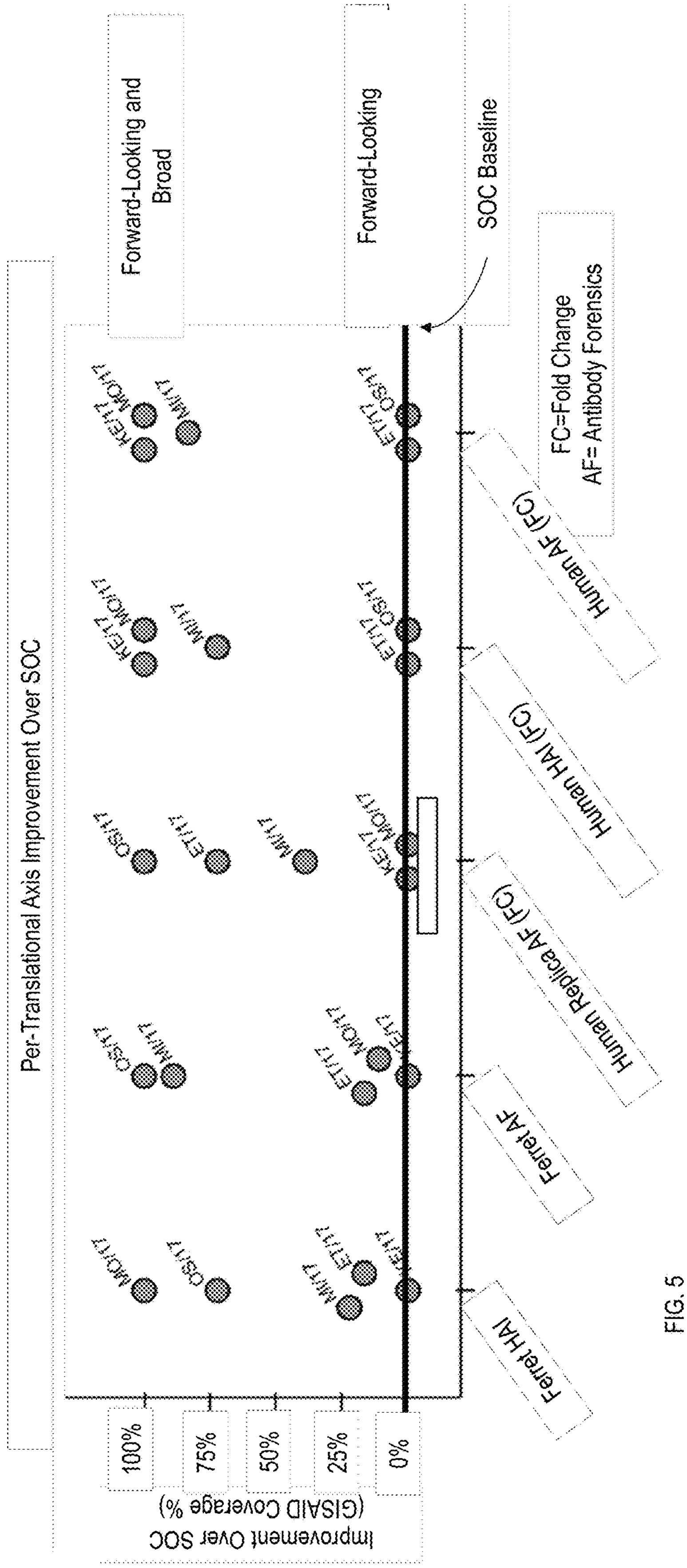
FIG. 5 shows a chart depicting the per-translational axis improvement over traditional techniques for designing vaccines.

FIG. 5 shows a chart depicting the per-translational axis improvement over traditional techniques for designing vaccines. In an example experiment, five (5) different vaccine candidates were selected by a particular instance of the previously described process (referred to by abbreviations MO/17, OS/17, MI/17, ET/17, and KE/17 which are cognate to strains A/MISSOURI/37/2017, A/OSORNO/60580/2017, A/MIYAZAKI/89/2017, A/ETHIOPIA/1877/2017, and A/KENYA/105/2017, respectively) and then evaluated against five (5) different translational axes (displayed across the x-axis) relative to a traditionally selected CV, A/SINGAPORE/INFIMH160019/2016. Each of the five different CVs selected by the systems and methods described in this specification are displayed as labeled markers for each of the translational axes, and jittered slightly within each translational axis for visual clarity. The y-axis indicates, for each translational axis, the fraction of March 2018 clinical isolates reported as of Apr. 15, 2018 (referred to as "seasonal proxy strains" in the sequel) in the Global Initiative on Sharing All Influenza Data (GISAID) global database, which were predicted to be better protected by a particular antigen than the traditionally selected CV (A/SINGAPORE/INFIMH160019/2016), which was the Standard Of Care (SOC) as of March 2018 for H3N2. For example, the leftmost column (Ferret HAI) shows that the translational model predicted that A/MISSOURI/37/2017 would raise antibodies in ferrets that have uniformly higher HAI titers against all of those seasonal proxy strains than the traditionally selected CV. As a further example, in the rightmost column (Human Sera Antibody Forensics (AF), A/ETHIOPIA/1877/2017 and A/OSORNO/60580/2017 were predicted to be noninferior to the traditionally selected CV. These results, taken together, suggested that these five candidates would exhibit diverse and differently noninferior patterns of elicited immune responses as assessed by different translational axes.

Figure 6:
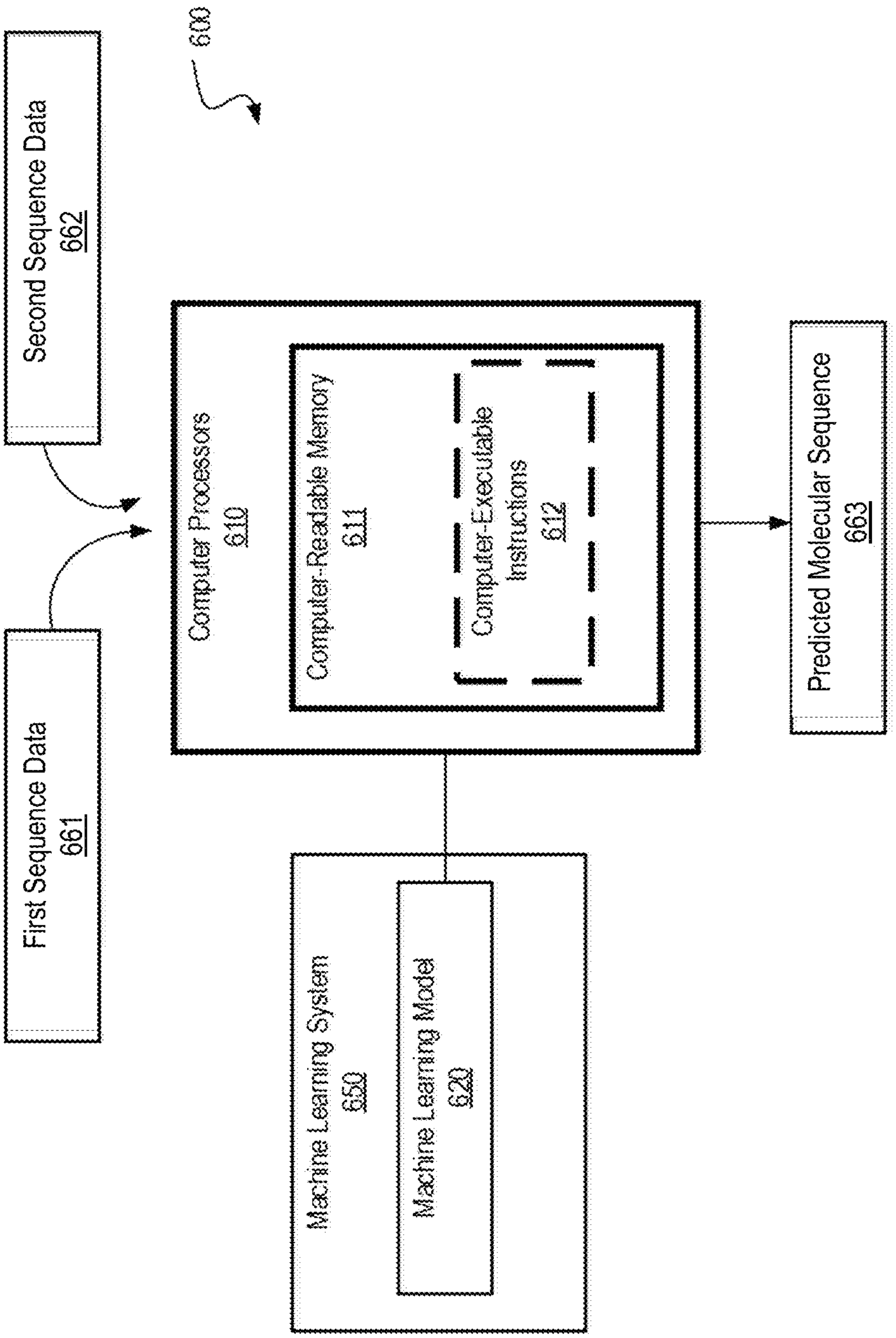
FIG. 6 shows an example of a system for predicting biological responses using machine learning techniques.

Example Translational Model:

FIG. 6 shows an example of a system 600 for predicting biological responses using machine learning techniques, in accordance with one or more embodiments of the present disclosure. The system 600 can be used as a translational model, as discussed previously. The system 600 includes computer processors 610. The computer processors 610 include computer-readable memory 611 and computer readable instructions 612. The system 600 also includes a machine learning system 650. The machine learning system 650 includes a machine learning model 620. The machine learning system 650 may be separate from or integrated with the computer processors 610.

The computer-readable memory 611 (or computer-readable medium) can include any data storage technology type which is suitable to the local technical environment, including, but not limited to, semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the computer-readable memory 611 includes code-segment having executable instructions.

In some implementations, the computer processors 610 include a general purpose processor. In some implementations, the computer processors 610 include a central processing unit (CPU). In some implementations, the computer processors 610 include at least one application specific integrated circuit (ASIC). The computer processors 610 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 610 are configured to execute program code means such as the computer-executable instructions 612. In some implementations, the computer processors 610 are configured to execute the machine learning model 620.

The computer processors 610 are configured to obtain first molecular sequence data 661 of a first molecular sequence and second molecular sequence data 662 of a second molecular sequence. The first molecular sequence data 661 can include amino acid sequence data of a candidate antigen (e.g., inoculation strain). The candidate antigen can correspond, for instance, to the H3N1 virus. The second molecular sequence data 662 can include amino acid sequence data of a known viral strain against which protection is sought. For instance, the second molecular sequence can be a known viral strain that occurred in the year 2001. In some implementations, as will be explained in further detail later with reference to FIG. 9, the computer processors 610 are also configured to receive non-human biological response data associated with the first and second molecular sequences. The non-human biological response data can include, for example, biological response readouts (e.g., antibody titers) that measure the biological response of a non-human model (e.g., mouse, ferret, human immune system replica, etc.) to the second molecular sequence after being inoculated with the first molecular sequence. As discussed later in further detail with reference to FIG. 9, in some implementations, the computer processors 610 are capable of encoding the first molecular sequence data 661 and the second molecular sequence data 662 as amino acid mismatches. The aforementioned data can be obtained through one or more means, such as wired or wireless communications with databases (including cloud-based environments), optical fiber communications, Universal Serial Bus (USB), compact disc read-only memory (CD-ROM), and so forth.

The machine learning system 650 applies machine learning techniques to train the machine learning model 620 that, when applied to the input data, generates indications of whether the input data items have the associated property or properties, such as probabilities that the input data items have a particular Boolean property, or an estimated value of a scalar property.

As part of the training of the machine learning model 620 the machine learning system 650 can form a training set of input data by identifying a positive training set of input data items that have been determined to have the property in question, and, in some implementations, forms a negative training set of input data items that lack the property in question.

The machine learning system 650 extracts feature values from the input data of the training set, the features being variables deemed potentially relevant to whether or not the input data items have the associated property or properties. An ordered list of the features for the input data is herein referred to as the feature vector for the input data. In some implementations, the machine learning system 650 applies dimensionality reduction (e.g., via linear discriminant analysis (LDA), principle component analysis (PCA), learned deep features from a neural network, or the like) to reduce the amount of data in the feature vectors for the input data to a smaller, more representative set of data.

In some implementations, the machine learning system 650 uses supervised machine learning to train the machine learning model 620 with the feature vectors of the positive training set and the negative training set serving as the inputs. Different machine learning techniques—such as linear support vector machine (linear SVM), boosting for other algorithms (e.g., AdaBoost), neural networks, logistic regression, naïve Bayes, memory-based learning, random forests, bagged trees, decision trees, boosted trees, or boosted stumps—are used in some implementations. The machine learning model 620, when applied to the feature vector extracted from the input data item, outputs an indication of whether the input data item has the property in question, such as a Boolean yes/no estimate, a scalar value representing a probability, a vector of scalar values representing multiple properties, or a nonparametric distribution of scalar values representing different and not a priori fixed numbers of multiple properties, which may be represented either explicitly or implicitly in a Hilbert or similar infinite dimensional space.

In some implementations, a validation set is formed of additional input data, other than those in the training sets, which have already been determined to have or to lack the property in question. The machine learning system 650 applies the trained machine learning model 620 to the data of the validation set to quantify the accuracy of the machine learning model 620. Common metrics applied in accuracy measurement include: Precision=TP/(TP+FP) and Recall=TP/(TP+FN), where precision is how many the machine learning model 620 correctly predicted (TP or true positives) out of the total it predicted (TP+FP or false positives), and recall is how many the machine learning model 620 correctly predicted (TP) out of the total number of input data items that did have the property in question (TP+FN or false negatives). The F score (F-score=2*PR/(P+R)) unifies precision and recall into a single measure. In some implementations, the machine learning system 650 iteratively re-trains the machine learning model 620 until the occurrence of a stopping condition, such as the accuracy measurement indication that the model 620 is sufficiently accurate, or a number of training rounds having taken place.

In some implementations, the machine learning model 620 includes a neural network. In some implementations, the neural network includes a convolutional neural network. The machine learning model 620 can include other types of neural networks, such as recurrent neural networks, radial basis function neural networks, physical neural networks (e.g., optical neural network), and so forth. Particular methods of training the machine learning model according to one or more implementations of the present disclosure are discussed later in more detail with reference to FIGS. 8-9.

The machine learning model 620 is configured to predict, based on the received data, a biological response 663 for the second molecular sequence. For example, assume that the first molecular sequence data 661 represents an amino acid sequence of a candidate antigen that is to be used as a vaccination and the second molecular sequence data 662 represents an amino acid sequence of a viral strain known to have been in circulation in the year 2012. The machine learning model 620 can predict a biological response (e.g., an antibody titer) that a human immune system will generate after encountering the second molecular sequence (e.g., known viral strain) if the human immune system was inoculated with the first molecular sequence (i.e., candidate antigen).

Figure 7:
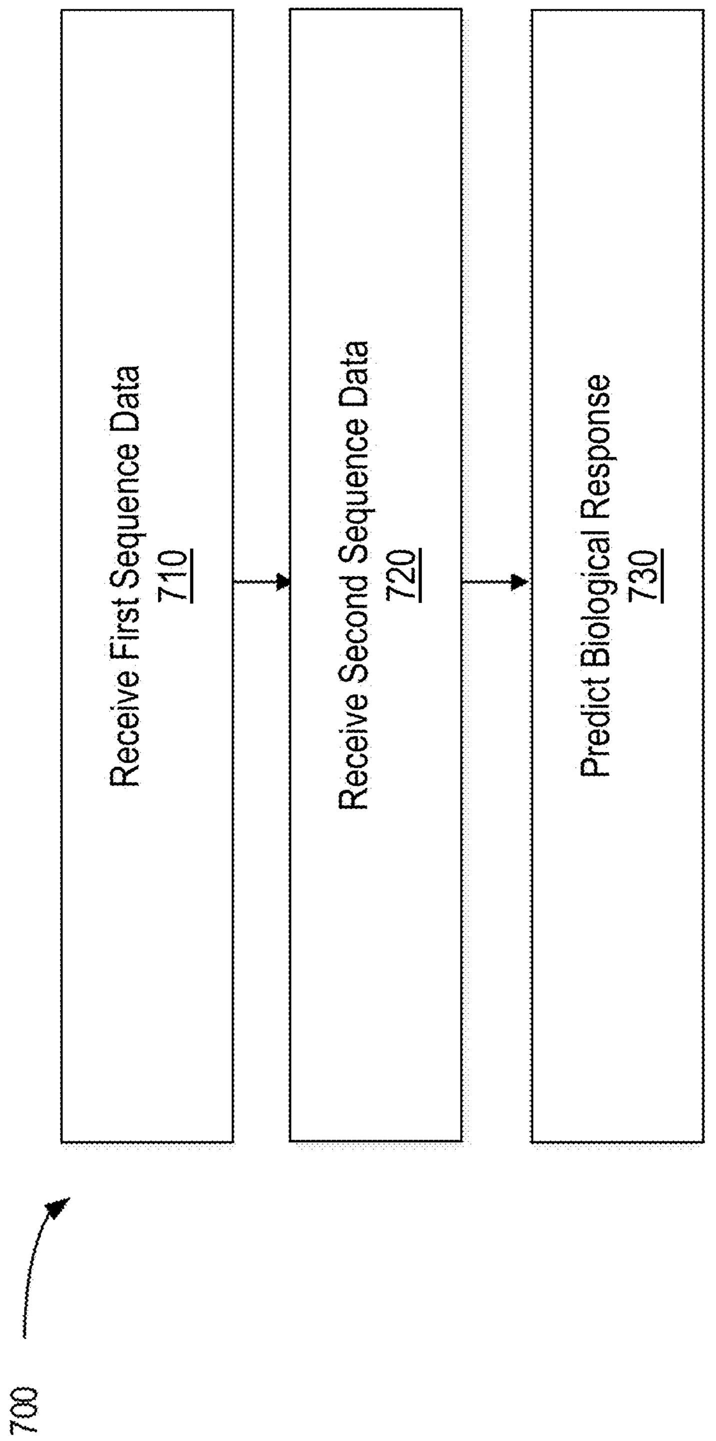
FIG. 7 shows a flowchart depicting an example of a method for predicting biological responses using machine learning techniques.

FIG. 7 shows a flowchart depicting an example of a method 700 for predicting biological responses using machine learning techniques, in accordance with one or more implementations of the present disclosure. For illustrative purposes, the method 700 is described as being performed by the system 600 for predicting biological responses using machine learning techniques discussed earlier with reference to FIG. 6. The method 700 includes receiving first sequence data of a first molecular sequence (block 710), receiving second sequence data of a second molecular sequence (block 720), and predicting a biological response for the second molecular sequence (block 730).

At block 710, the computer processors 710 receive the first molecular sequence data 161 of the first molecular sequence. As previously indicated, the first molecular sequence data 161 can include amino acid sequence data of a candidate antigen (e.g., inoculation strain). For instance, the candidate antigen can correspond to the H3N1 virus.

At block 720, the computer processors 720 receive the second molecular sequence data 662 of the second molecular sequence. The second molecular sequence data 662 can include amino acid sequence data of a known viral strain against which protection is sought. For instance, the second molecular sequence can be a known viral strain that occurred in the year 2001.

In some implementations, the method 700 further includes encoding the first molecular sequence data 661 and the second molecular sequence data 662 as amino acid mismatches. For example, similar regions of the first molecular sequence and the second molecular sequence can be compared, and a value of "1" can be encoded for each non-matching amino acid pairing in the regions, while a value of "0" can be encoded for each matching amino acid pairing in the region. Thus, the dissimilarity between the first molecular sequence and the second molecular sequence, as defined by non-matching amino acids at locations within a similar region between the molecular sequences, can be provided to the machine learning model 620.

In some implementations, the method 700 further includes receiving non-human biological response data associated with the first and second molecular sequences. The non-human biological response data can include, for example, biological response readouts (e.g., antibody titers) that measure the biological response of a non-human model (e.g., mouse, ferret, replica human immune systems, etc.) to the second molecular sequence after being inoculated with the first molecular sequence.

At block 730, the machine learning model 620 predicts a biological response for the second molecular sequence based on the received data. For example, the machine learning model 620 can predict a biological response (e.g., an antibody titer) that a human immune system will generate after encountering the second molecular sequence (i.e., known viral strain) if the human immune system was inoculated with the first molecular sequence (i.e., candidate antigen). In some implementations, the machine learning model 620 is configured to predict a non-human biological response for the second molecular sequence. For instance, the machine learning model can predict an antibody titer that an animal's immune system (e.g., mouse, ferret, etc.) will generate after encountering the second molecular sequence if the animal's immune system was inoculated with the first molecular sequence.

Methods of Training Machine Learning Models for Predicting Biological Responses:

Methods for training the machine learning model 620 to predict biological responses will now be described. FIG. 8 shows an example of data used to train a machine learning model for predicting biological responses, in accordance with one or more implementations of the present disclosure. As shown, data from thousands (or millions, billions, etc.) of experiments can be used to build a comprehensive repository of biological response readouts and viral sequence data from, for example, ferret, mouse, and in vitro human immune system replica (e.g., MIMIC®) models. In the shown embodiment, the data includes antigen sequence data, viral sequence data, and biological response readouts as measured by hemagglutination inhibition assay (HAI) and antibody forensics (AF). The viral sequence data includes a panel of known viral strains (referred to as a "read-out" panel). The experiments can be separated into batches referred to as "cycles" (e.g., cycle 1 and cycle 2). In each cycle, the model systems are challenged with selected molecular sequences (e.g., H3 proteins, vaccine preparations, etc.) and measured for their ability to generate an immune response against a panel of "read-out" viral strains (referred to as a "read-out panel"). The viral read-out panels can be selected to represent a broad sampling of influenza strains that were in circulation during a defined period of years (e.g., 1950 to 2016).

To associate the model experiments with human results, human sera can be measured against the "read-out" panel. In the shown example, for every pair of antigen-strain/readout-strain tested in the model systems, there is not always a corresponding pair in the human serum measurements. This is because human samples may be collected from people vaccinated during periods that don't cover the full period of years used for each of the cycles. Accordingly, the machine learning model can be restricted to only the antigens and readouts tested in human sera, and a vector of human readout titers can be selected as the target vector for the machine learning model. The human AF readouts can be from human sera collected at Day 21 post-vaccination, which is usually sufficient time for a subject to seroconvert after inoculation.

Using the resulting data from the aforementioned experiments, a model can be trained to predict biological responses. In some implementations, a linear model can be used.

Figure 9:
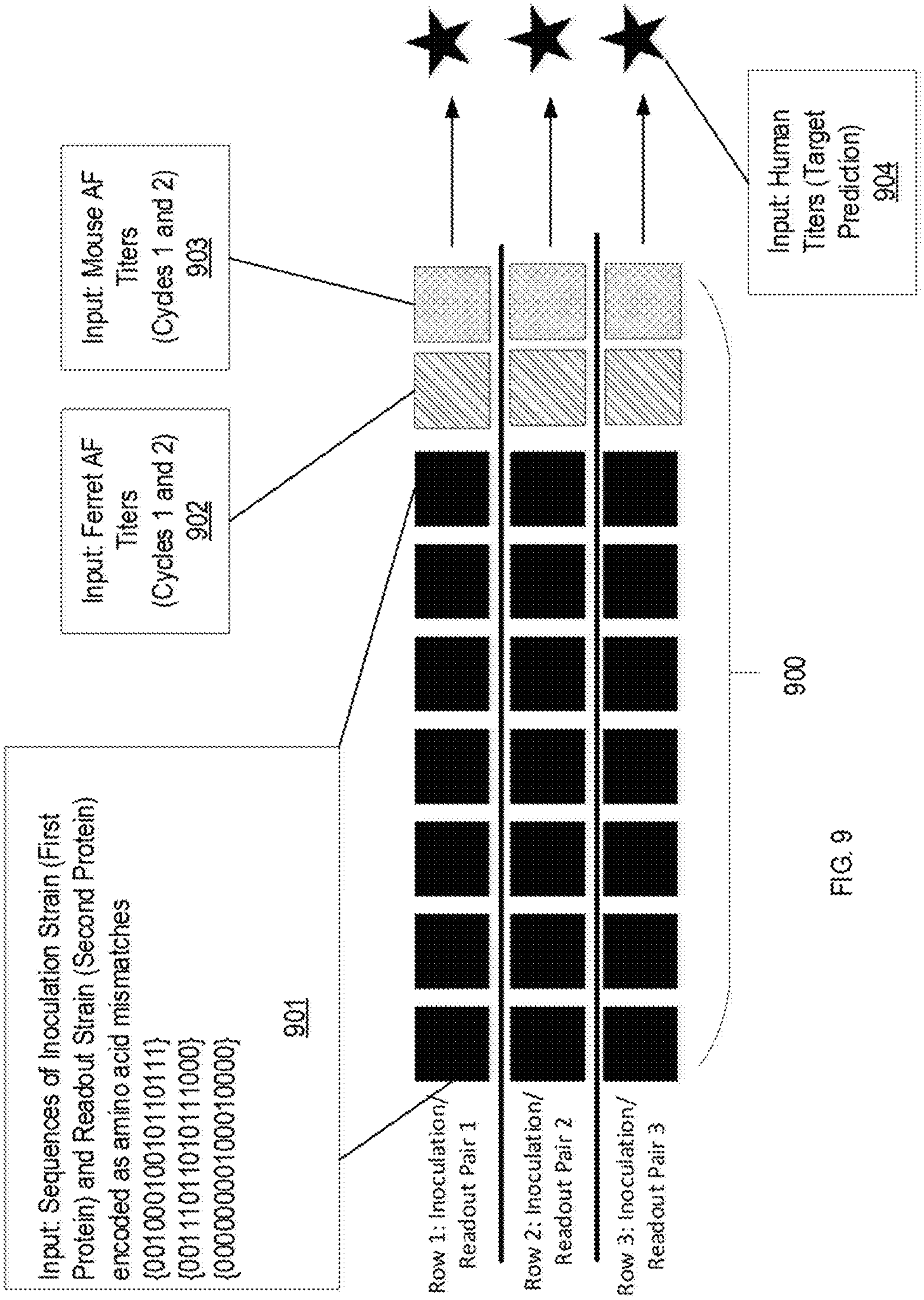
FIG. 9 shows a flow diagram of an example for training a machine learning model for predicting biological responses.

FIG. 9 shows a flow diagram of an example for training a machine learning model for predicting biological responses, in accordance with one or more implementations of the present disclosure. As shown, a data matrix 900 is first prepared where each row corresponds to a pair of virus antigens, such as the H3 regions of the antigen strain and the "read-out" strain. The columns (or features) of the matrix include specific columns for the ferret model AF readout titers 902 and the mouse model AF readout titers 903. In some implementations, missing titer data is imputed with the mean value of the column. However, any number of standard methods may be used to impute missing titer data. The sequence columns 901 represent an amino acid sequence difference (SeqDiff) representation between the antigen strain and "read-out" strain in a selected region, which in the shown example includes the H3 regions of the antigen and "read-out" strain. A SeqDiff is prepared by checking, at each position of an H3 amino acid sequence alignment, whether the amino acid is the same or different between the antigen and "read-out" strain. If the amino acids between the two strains are not the same, a "1" can be encoded. If the amino acids between the two strains are the same, a "0" can be encoded. Encoding the two sequences as amino acid mismatches can essentially create a protein hamming distance measure, which generally reflects the number of positions at which the corresponding amino acids are different. In some implementations, columns that are consistently "0" across the entire training set are discarded. The columns 901, 902, 903 of each row are associated with a corresponding human titer 904 using linear regression.

Columns 902, 903 including readout titers can be, for example, z-score transformed before fitting a linear regression model. Z-scores can refer to linearly transformed data values having a mean of zero and a standard deviation of one, and can indicate how many standard deviations an observation is above or below the mean. Because the encoding of the SeqDiff representation can be sparse, in some instances, Principle Component Analysis (PCA) can be used to reduce the dimensionality of the SeqDiff vectors to five components. PCA refers to a statistical procedure that uses an orthogonal transformation to convert a set of observations of possibly correlated variables into a set of values of linearly uncorrelated variables called principal components. PCA can be used to emphasize variation, highlight strong patterns in datasets, and reduce a large set of variables to a smaller set without losing a significant amount of information in the larger set. The linear model can be trained on various combinations of the data to better understand the relative abilities of mouse titers, ferret titers, and sequence data to predict human responses.

While, as previously described, the machine learning model can be built as a linear model to predict the biological responses, it is possible that non-linear relationships exist between the data features and the human biological responses. Accordingly, using the data from the aforementioned experiments, a model using a deep neural network, or other nonlinear models, can be built that is capable of 1) leveraging non-linear relationships in the data to make relatively accurate predictions when compared to the aforementioned linear model and 2) making predictions for both animal and human titers simultaneously. Predicting all titers together can exploit the realization that a strong signal for immune response may be encoded directly in the protein sequences of the antigen & "read-out" strains. By training the model to predict both human and animal titers from sequence alone, the machine learning model can be forced to search for sequence-function relationships that drive immunogenicity across species. In statistical terms, this may be referred to as "borrowing strength," and can allow the model to better leverage large amounts of available data for one type of model (e.g., ferret model) to generate more robust predictions for human responses. This strategy can accommodate more viral antigens and the building of a data matrix with over 13000 example rows. As with the linear models, the SeqDiff representation of the H3 regions for each viral and readout strain pair can be used as input data.

While, in some implementations, the target vector is human titers for the linear model, the non-linear neural network model can represent a multi-target regression problem with, for example, seven output columns (Ferret HAI & AF titers, Mouse HAI and AF titers, MIMIC AF, Human HAI, Human AF). Because the limit of detection for HAI experiments may typically be 40 (or, when expressed as a dilution, 1:40), any measurements falling below this value can be set to 40. Similarly, AF measurements can be set to 10000 if they fall below that value. HAI can be expressed as log 2(titer/10), while AF can be expressed as log 2(titer). Human and human replica data may have an extra level of complexity if measurements are made at the time of inoculation (Day0) and post-seroconversion (Day21). Accordingly, human and human replica titers can be expressed as a log 2 fold-change of Day 21/Day0. In cases where titer values are missing in the target vectors, those values can be set to zero and the loss function in the neural network can be masked for those positions. This can ensure that predictions for missing values do not contribute to the fitness of the model during training.

In some implementations, a neural network having two 128-node dense layers with relu activation, and a 7-node dense output layer can be used. Portions of the data (for example, fifteen percent of the data) can be randomly excluded as a test set and the neural network network can be trained for a number of epochs (for example 400, 500, 1000, etc.). In some implementations, the following parameters are used: learning rate=0.001; weight-decay=0.0001; batch size=128.

In some implementations, an L2 loss function is used for human replica, human AF, and human HAI target vectors. Generally, an L2 loss function minimizes the squared differences between the estimate target values and the existing target values. In some implementations, a Huber loss function can be used for ferret and mouse data. Generally, a Huber loss function is used in robust regression, and, in at least some instances, can be less sensitive to outliers in data than the L2 loss function. To further bias the model, an explicit weighting scheme can be used to apply an additional penalty to misclassified human samples. For example, the following weights can be multiplied by each target loss at each epoch of training: Ferret HAI=0.8; Ferret AF=1; Mouse HAI=1; Mouse AF=1; Human HAI=2; Human AF=2; MIMIC=1.5.

While the foregoing description may sometimes describe a pathogenic strain in the context of an influenza strain for illustrative purposes, the term pathogenic is construed broadly to encompass any infectious agent. For example, a pathogenic strain can refer to a viral strain, a bacterial strain, a protozoan strain, a prion strain, a viroid strain, or a fungal strain, among others. A pathogenic stain can correspond to the respiratory syncytial virus, and other paramyxoviruses. A pathogenic strain can correspond to Pertussis, Diphtheria, or Tetanus, among others.

While the foregoing description may sometimes describe a pathogenic season in the context of an influenza season, the term pathogenic season is construed broadly to encompass any discrete interval of time. For example, a pathogenic season can refer to a particular month, a particular week, a particular series of weeks, a particular series of months, a particular series of days, among others. Furthermore, consecutive pathogenic seasons can be consistent or vary. For example, two consecutive pathogenic seasons can both be one month in length, or one pathogenic season can be one month in length while the second pathogenic season can be 4 days in length.

While the foregoing description describes certain translational axes/biological responses, such as Ferret HAI titers and Mouse AF titers, implementations are not so limited. For example, a biological response/translational axis can correspond to antibody characterizations, such as affinity and/or avidity against specific antigens and/or panels of antigen fragments (e.g. protein arrays, phage display libraries, and the like), functional profiling such as to determine anti-drug-antibodies, immune complement interaction (e.g. phagocytosis, inflammation, membrane attack), antibody-dependent cellular cytotoxicity (ADCC) or similar Fc-mediated effector functions, profiling of immune complexes formed (e.g. receptor-binding profiles), immunoprecipitation assays, or combinations of these. A biological response/translational axis can correspond to competition of an antibody binding to a target by other antibodies, or antisera. A biological response/translational axis can correspond to antisera characterizations, which can correspond to those of the aforementioned antibody characterizations, and functional assays (such as microneutralization assays, hemagglutination inhibition, and neuraminidase inhibition), binding assays (such as hemagglutination assays), enzymatic reaction assays (such as enzyme-linked lectin assays (ELLA)), ligand binding assays (such as binding of sialic acid derivatives and their mimetics), and fluorescent readout assays (such as 20-(4-methylumbelliferyl)-a-D-N-acetylneuraminic acid (MUNANA) cleavage).

A biological response/translational axis can correspond to in vivo assessments leveraging either monoclonal or polyclonal antibodies through passive transfer and/or exogenous expression or transfer achieved by one or more of the following: transfection or endogenous expression mediated by retroviral infection, or host genome modification such as through CRISPR, fluid transfer between two bodies, or combinations of these. A biological response/translational axis can correspond to in vivo assessments of immunity raised through immunization to assess antigenicity. A biological response/translational axis can correspond to characterizations such as binding/affinity measurements of linear peptide antigens on major histocompatibility complex (MHC) class I and class II), and also to assess productive T-cell epitope display for recognition by T-cells. A biological response/translational axis can correspond to characterizations such as affinity against panels of antigen fragments (e.g. protein arrays, phage display libraries, and the like) to identify epitopes being recognized. A biological response/translational axis can correspond to functional profiling ex vivo and/or in vitro such as to determine T-cell responses and/or responses mediated. A biological response/translational axis can correspond to in vivo and/or in situ measurements of proliferation (e.g. abundance in tissue compartments) in response to natural infection and/or challenge and/or immunization of adaptive-response associated T-cells (e.g. $\alpha\beta$ or $\gamma\delta$ T-cells). A biological response/translational axis can correspond to in vitro and/or ex vivo measurements of specificity in recognition by adaptive-response associated T-cells (e.g. $\alpha\beta$ or $\gamma\delta$ T-cells) in response to natural infection and/or challenge and/or immunization as measured by competition with other epitopes.

A biological response/translational axis can correspond to in situ, ex vivo and/or in vivo assessments of morphology or physiological changes to tissue formation, tissue repair, or tissue invasion by a pathogen to be protected against or a proxy such as pseudotyped viruses or bacteria. A biological response/translational axis can correspond to in situ, ex vivo protein, gene expression, and/or non-coding RNA level differences relative to other antigens and/or physiological status as characterized, for example, by biomarkers such as age, gender, frailty, nominal serostatus, race, haplotype, geographic location. A biological response/translational axis can correspond to in situ assessments of protection, transmission, or other gross physiological responses to infection either naturally occurring or through transmission in humans or model organisms such as, but not restricted to mouse, rat, rabbit, ferret, guinea pig, pig, cow, chicken, sheep, porpoises, bat, dog, cat, zebrafish and other teleosts, and non-human primates such as monkeys and great apes.

With respect to response deliberate infection (i.e. challenge) with homotypic and/or heterotypic infectious agents, including in controlled human challenge studies, a biological response/translational axis can correspond to in situ, ex vivo, and/or in vivo assessments of proteins or metabolites present in blood or tissues, in which the proteins may be cytokines, hormones, or signaling molecules, and in which the metabolites may be vitamins, cofactors, or other metabolic by-products. A biological response/translational axis can correspond to in situ, ex vivo, and/or in vivo assessments of a microbiome that may be affected by or impact the immune response. A biological response/translational axis can correspond to functional profiling ex vivo, in vitro phenotypic, and/or functional T-cell response profiling (receptor expression, cytokine production, cytotoxic potential) in response to challenge with antigen alone or antigen in conjunction with innate immune cells (such as natural killer (NK) cells, dendritic cells (DCs), neutrophils, macrophages, monocytes, and so forth). A biological response/translational axis can correspond to epigenetic analysis performed using samples collected or generated using techniques or methods as previously described.

While the foregoing description describes certain methods and data for training a machine learning model to predict biological responses, other methods and data can be used. For example, the neural network model can include more or fewer layers than the models previously described, where each layer can have more or less nodes.

In the foregoing description, implementations have been described with reference to numerous specific details that may vary from implementation to implementation. The description and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising," in the foregoing description or following claims, what follows this phrase can be an additional step or entity, or a sub-step/sub-entity of a previously-recited step or entity.

What is claimed is:

1. A method for synthesizing a vaccine against influenza that provides protection across multiple influenza strains, the method comprising:

obtaining, by one or more computers, an influenza temporal sequence data set that comprises, for each of a plurality of molecular sequences, data defining: (i) the molecular sequence, and (ii) one or more times of circulation for a plurality of influenza strains, wherein each of the one or more influenza strains include the molecular sequence as a natural antigen;

training, by the one or more computers, a driver neural network model using a machine learning training technique by, at each of a plurality of training iterations, performing operations comprising:

i) processing the influenza temporal sequence data set by the driver neural network model, in accordance with current values of a set of parameters of the driver neural network model, to generate output data representing one or more candidate molecular sequences;

ii) for each candidate molecular sequence generated by the driver neural network model at the training iteration and for each of a plurality of target influenza strains, jointly processing data defining: (a) the candidate molecular sequence, and (b) a molecular sequence of the target influenza strain, by a translational machine learning model to generate a biological response score that defines a predicted biological response of an entity vaccinated with a vaccine having an antigen with the candidate molecular sequence to the target influenza strain;

iii) determining, for each candidate molecular sequence and based on the biological response scores for the plurality of target influenza strains, a number of the target influenza strains for which vaccinating an entity with the candidate molecular sequence is predicted to achieve at least a threshold biological response in the entity; and iv) adjusting the current values of the set of parameters of the driver neural network model, by the machine learning training technique, to optimize a loss function that depends on the biological response score for each candidate molecular sequence generated by the driver neural network model at the training iteration, wherein the loss function depends on, for each candidate molecular sequence, the number of target influenza strains for which vaccinating the entity with the candidate molecular sequence is predicted to achieve at least the threshold biological response in the entity;

wherein steps (i), (ii), (iii), and (iv) are performed by the one or more computers at each of the plurality of training iterations;

after training the driver neural network model by performing steps (i), (ii), (iii), and (iv) at each of the plurality of training iterations by the one or more computers, processing the influenza temporal sequence data set using the trained driver neural network model to generate an antigenic molecular sequence;

physically synthesizing a vaccine having an antigen with the antigenic molecular sequence generated by the driver neural network model.

2. The method of claim 1, wherein the driver neural network model includes a recurrent neural network.

3. The method of claim 1, wherein the driver neural network model includes a long short-term memory recurrent neural network.

4. The method of claim 1, wherein the output data representing one or more candidate molecular sequences comprises one or more candidate molecular sequences for each of a plurality of influenza seasons.

5. The method of claim 4, wherein for each of the plurality of influenza seasons, the candidate molecular sequences corresponding to the influenza season are predicted to achieve a maximized aggregate biological response across all influenza strains in circulation for the influenza season.

6. The method of claim 4, wherein for each of the plurality of influenza seasons, the candidate molecular sequences corresponding to the influenza season are predicted to generate a biological response that will effectively immunize against a maximized number of influenza strains in circulation for the influenza season.

7. The method of claim 1, wherein the entity is: a ferret, a mouse, a human replica, or a human.

8. The method of claim 1, wherein the training of the driver neural network model is performed for a predetermined number of training iterations.

9. The method of claim 1, wherein the training of the driver neural network model is performed until a termination criterion based on a predetermined error value is satisfied.

10. The method of claim 1, wherein for each candidate molecular sequence, the predicted biological response of the entity vaccinated with the candidate molecular sequence characterizes a predicted biological response measured by a hemagglutination inhibition assay.

11. The method of claim 1, wherein for each candidate molecular sequence, the predicted biological response of the entity vaccinated with the candidate molecular sequence characterizes a predicted biological response measured by an enzyme-linked immunosorbent assay.

12. The method of claim 1, wherein each candidate molecular sequence defines a respective antigen.

13. The method of claim 1, further comprising, for each candidate molecular sequence:

generating an aggregate biological response score by aggregating the respective biological response score for each of the plurality of target influenza strains;

wherein the loss function depends on the respective aggregate biological response score for each candidate molecular sequence.

14. The method of claim 13, wherein for each candidate molecular sequence, generating the aggregate biological response score comprises:

determining an average of the biological response scores.

15. The method of claim 1, wherein training the driver neural network model comprises training an ensemble of driver neural network models; and wherein the method further comprises:

selecting a proper subset of the ensemble of driver neural network models having highest performance measures from among the ensemble of driver neural network models; and selecting the antigenic molecular sequence for the vaccine using the proper subset of the ensemble of driver neural network models.

16. The method of claim 1, further comprising:

experimentally evaluating a performance of the vaccine having the antigen with the antigenic molecular sequence using real-world physical experiments.

17. The method of claim 1, wherein each candidate molecular sequence generated by the driver neural network model at the training iteration comprises a respective candidate molecular amino acid sequence;

wherein for each of the plurality of target influenza strains, the molecular sequence of the target influenza strain comprises an amino acid sequence of the target influenza strain; and wherein for each candidate molecule sequence generated by the driver neural network model at the training iteration and for each of the plurality of target influenza strains, jointly processing data defining: (i) the candidate molecular sequence, and (ii) the molecular sequence of the target influenza strain, comprises:

jointly processing data identifying amino acid mismatches between corresponding positions in the candidate molecular amino acid sequence and the amino acid sequence of the target influenza strain.

18. The method of claim 1, wherein the translational machine learning model is parametrized by a set of translational machine learning model parameters having respective values that have been determined by a second machine learning training technique.

19. The method of claim 1, wherein the translational machine learning model comprises a recurrent neural network.

* * * * *